United States Patent
Gu et al.

(10) Patent No.: US 11,294,171 B2
(45) Date of Patent: Apr. 5, 2022

(54) LIGHT SENSING METHOD, PHYSIOLOGICAL PARAMETER COMPUTING METHOD AND LIGHT SENSING SYSTEM

(71) Applicant: PixArt Imaging Inc., Hsin-Chu (TW)

(72) Inventors: Ren-Hau Gu, Hsin-Chu (TW); Chih-Hsin Lin, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 130 days.

(21) Appl. No.: 16/840,477

(22) Filed: Apr. 6, 2020

(65) Prior Publication Data
US 2020/0233210 A1 Jul. 23, 2020

Related U.S. Application Data

(62) Division of application No. 15/672,312, filed on Aug. 9, 2017, now Pat. No. 10,649,206.

(30) Foreign Application Priority Data

Jan. 25, 2017 (TW) .................................. 106102771

(51) Int. Cl.
  *G02B 27/00* (2006.01)
  *A61B 5/00* (2006.01)
  (Continued)

(52) U.S. Cl.
  CPC ...... *G02B 27/0025* (2013.01); *A61B 5/02438* (2013.01); *A61B 5/14551* (2013.01);
  (Continued)

(58) Field of Classification Search
  CPC ............ G02B 27/0025; A61B 5/14551; A61B 5/7203; A61B 5/681
  (Continued)

(56) References Cited

U.S. PATENT DOCUMENTS

| 10,420,470 | B2 | 9/2019 | Kwon | |
| 2016/0113530 | A1* | 4/2016 | Nagahiro | A61B 5/6843 600/473 |
| 2016/0206212 | A1* | 7/2016 | Lee | A61B 5/6801 |

FOREIGN PATENT DOCUMENTS

| CN | 104270582 A | 1/2015 |
| CN | 105832307 A | 8/2016 |

(Continued)

*Primary Examiner* — Amanda K Hulbert
*Assistant Examiner* — Philip C Edwards
(74) *Attorney, Agent, or Firm* — Winston Hsu

(57) ABSTRACT

A light sensing method, applied to a light sensing system comprising a light sensor and at least one light source. The light sensor comprises a plurality of light sensing units. The light sensing method comprises: controlling the light sensor to capture images according to the light source; generating an exposure condition according brightness that each of the light sensing units senses, to control all the light sensing units to generate a target brightness distribution according to the exposure condition; and controlling the light sensing units to sense light from the light source according to the exposure condition. The light sensing system can have a better SNR via adjusting the exposure condition for each one of the light sensing units. Such light sensing method can be applied to compute physiological parameters.

3 Claims, 6 Drawing Sheets

(51) Int. Cl.
*A61B 5/024* (2006.01)
*A61B 5/1455* (2006.01)

(52) U.S. Cl.
CPC ............ *A61B 5/681* (2013.01); *A61B 5/7203* (2013.01); *A61B 5/02433* (2013.01); *A61B 5/6824* (2013.01); *A61B 5/7214* (2013.01); *A61B 2562/046* (2013.01)

(58) Field of Classification Search
USPC ........................................................ 600/509
See application file for complete search history.

(56) References Cited

FOREIGN PATENT DOCUMENTS

| CN | 106308776 A | 1/2017 |
|---|---|---|
| WO | 2016/096409 A1 | 6/2016 |

\* cited by examiner

LIGHT SENSING METHOD, PHYSIOLOGICAL PARAMETER COMPUTING METHOD AND LIGHT SENSING SYSTEM

CROSS REFERENCE TO RELATED APPLICATIONS

This application is a division of applicant's earlier U.S. application, Ser. No. 15/672,312, filed 2017 Aug. 9, which claims the benefit of TWN application, Serial No. 106102771, filed 2017 Jan. 25. The contents thereof are included herein by reference.

BACKGROUND OF THE INVENTION

1. Field of the Invention

The present invention relates to a light sensing method, a physiological parameter computing method, and a light sensing system, and particularly relates to a light sensing method, a physiological parameter computing method, and a light sensing system which can increase a SNR (Signal to Noise Ratio).

2. Description of the Prior Art

In recent years, people pay more attention to their health. Accordingly, a wearable device which can measure a heart rate becomes more and more popular. Conventionally, a heart rate measuring method uses a light source to emit light to a part of a human body, such as a finger or a wrist, and then measures light reflected from the human body. By this way, the heart rate can be acquired. The reason is: the blood amounts in the artery are different during contraction of heart and during relaxation of heart, thus the absorbing levels for blood in the artery are also different during contraction of heart and during relaxation of heart. Accordingly, the heart rate can be acquired via measuring the reflection levels for the light.

However, the distances between light sources and light sensing units for a light sensor are different. Therefore, the same light source will cause different light response for different light sensing units in the same light sensor. Thus, the SNR for light sensing signals is reduced, and the measuring for the heart rate is non-accurate.

SUMMARY OF THE INVENTION

Therefore, one objective of the present invention is to provide a light sensing method and a light sensing system, which can cause a higher SNR while the light sensor sensing light.

Another objective of the present invention is to provide a more accurate physiological parameter computing method.

Another embodiment of the present invention provides a light sensing method, applied to a light sensing system comprising a light sensor and at least one light source. The light sensor comprises a plurality of light sensing units. The light sensing method comprises: controlling the light sensor to capture images according to the light source; generating an exposure condition according brightness that each of the light sensing units senses, to control all the light sensing units to generate a target brightness distribution according to the exposure condition; and controlling the light sensing units to sense light from the light source according to the exposure condition.

Another embodiment of the present invention provides a physiological parameter computing method applied to a physiological parameter computing system comprising a light sensing system including a plurality of light sensing units and at least one light source. The physiological parameter computing comprises: controlling the light sensor to capture images according to the light source; generating an exposure condition according brightness that each of the light sensing units senses, to control all the light sensing units to generate a target brightness distribution according to the exposure condition; and controlling the light sensing units to sense light from the light source according to the exposure condition.

Another embodiment of the present invention provides a light sensing system comprising: a plurality light sensing units; at least one light source; and a processing unit, configured to generate an exposure condition according brightness that each of the light sensing units senses, to control all the light sensing units to generate a target brightness distribution according to the exposure condition; wherein the light sensing units sense light from the light source according to the exposure condition.

In view of above-mentioned embodiments, the exposure conditions for each of the light sensing units can be adjusted to cause the light source to provide a proper light response to the light sensor. By this way, the SNR can be raised, and the accuracy for computing a physiological parameter can be increased as well. Additionally, the present invention further provides a power saving mode to save power consumption.

These and other objectives of the present invention will no doubt become obvious to those of ordinary skill in the art after reading the following detailed description of the preferred embodiment that is illustrated in the various figures and drawings.

DETAILED DESCRIPTION

In following descriptions, a plurality of embodiments are provided to explain the concept of the present invention. Please note, each apparatus, system, device or module illustrated in following embodiments can be implemented by hardware (ex. circuit) or hardware with software (ex. program installed to a processing unit). Besides, the name, the number or the location for elements in each embodiment is only for example and does not mean to limit the scope of the present invention.

Figure 1:
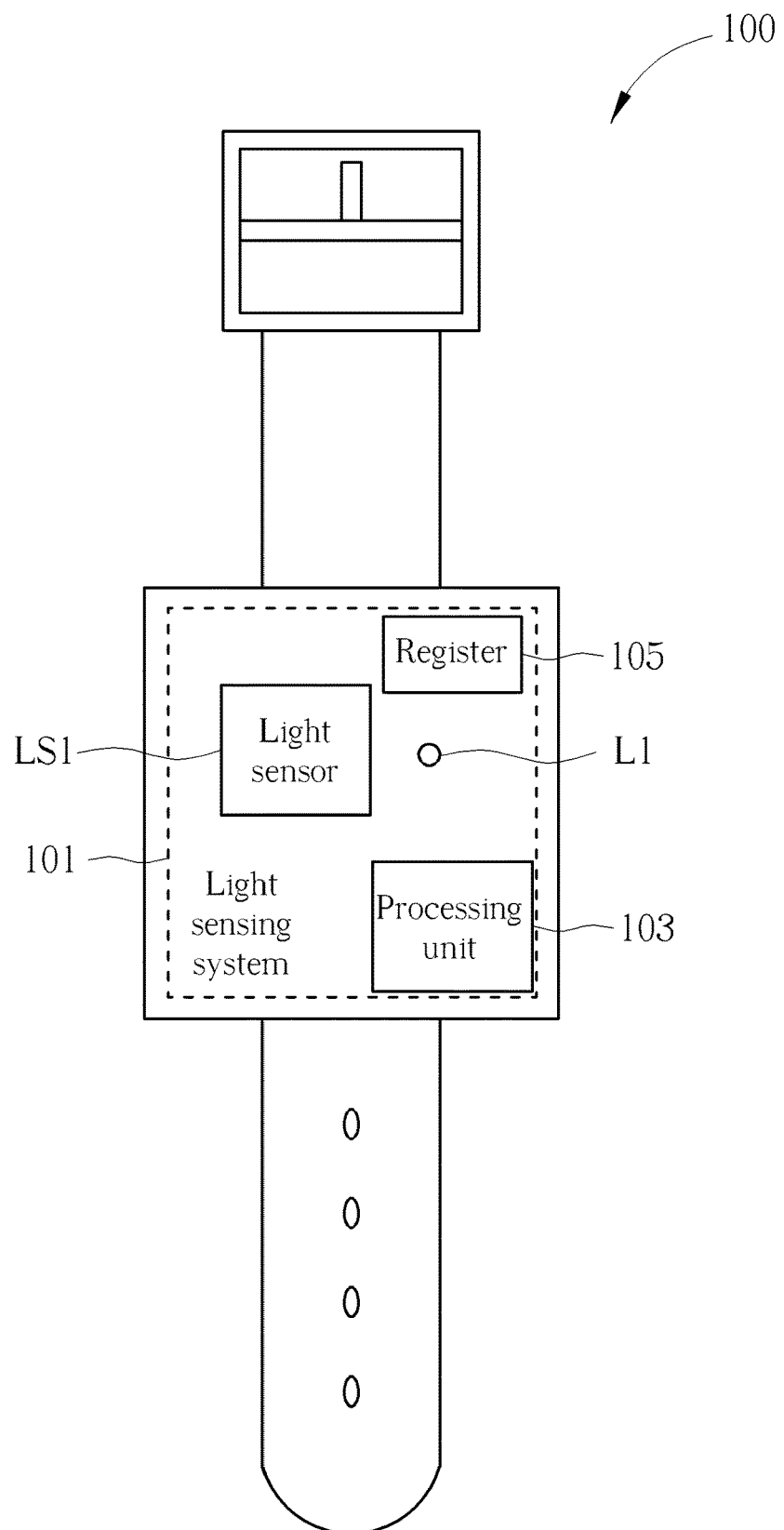
FIG. 1 is a schematic diagram illustrating a light sensing system according to one embodiment of the present invention.

FIG. 1 is a schematic diagram illustrating a light sensing system according to one embodiment of the present invention. As illustrated in FIG. 1, the wearable apparatus 100 comprises a light sensing system 101, which comprises a light senor LS1, at least one light source (in this embodiment, one light source L1, but not limited) and a processor 103. In one embodiment, the light senor LS1 is a light sensing diode matrix, and the light source can be a light emitting diode or a laser light source. In one embodiment, the light source can emit light having single wavelength (ex. an infrared light source, or green light source) to increase the sensing efficiency of the light sensor LSI.

The light sensor LSI comprises a plurality of light sensing units (ex. a light sensing diode or a group of light sensing diodes, not illustrated here). The processing unit 103 respectively controls an exposure condition for each of the light sensing units according distances between each one of the light sensing units and the light source L1, and controls the light sensing units to sense the light from the light source according to the exposure condition. The exposure condition can be: a light sensing time of a light sensing unit, a light sensing frequency of a light sensing unit or a read signal gain value. The read signal gain value means a gain value for light sensing signals read from light sensing units. Therefore, if a constant light response is desired for a light sensing unit far from the light source L1, a stronger exposure condition is needed. For example, increase the light sensing time, the light sensing frequency, or the read signal gain value.

In one embodiment, the exposure condition is computed according to a distance between the light source and the light sensing unit, and then the exposure condition is stored to a register 105. The light sensor LS1 reads the exposure condition from the register 105 before capture an image. In one embodiment, the register 105 can pre-store a predetermined exposure condition, which can be decided by other factors rather than a distance between the light source and the light sensing unit. After that, the exposure condition decided according to a distance between the light source and the light sensing unit can be updated to replace the predetermined exposure condition.

In one embodiment, the light sensing system 101 can operate in a calibrating mode. In the calibrating mode, the processing unit 103 adjusts the exposure condition according to the sensed brightness, after the light sensor LSI captures an image according to light from the light source L1, thereby all the light sensing units can generate a target brightness distribution according to the adjusted exposure condition. The target brightness distribution can be any kinds of brightness distribution. For example, the target brightness distribution can be a uniform brightness distribution, which means brightness difference for neighboring light sensing units or the difference between the maximum brightness and the minimum brightness for all light sensing units is lower than a threshold value. The new exposure condition is updated to the register 105 after acquired.

Figure 2:
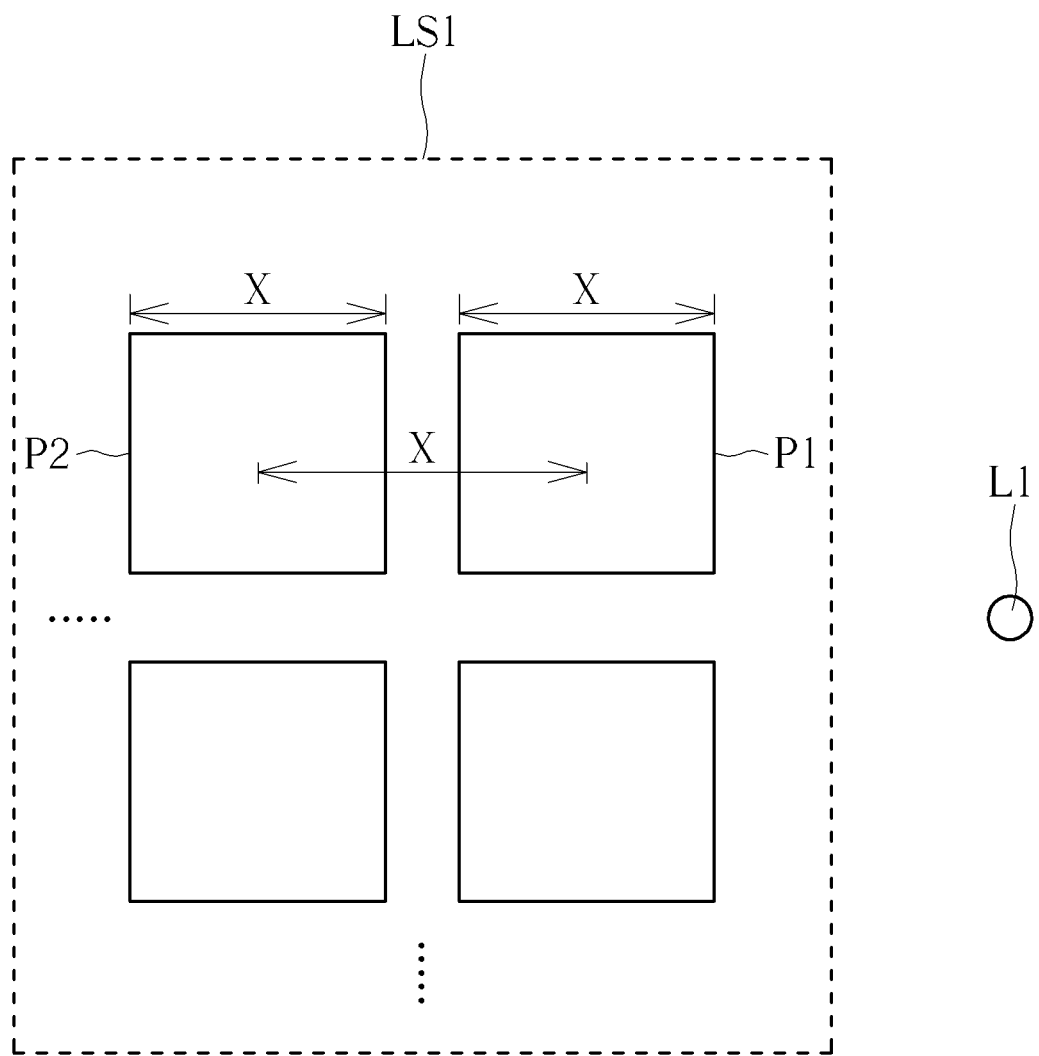
FIG. 2 is a schematic diagram illustrating a more detail light sensing system according to one embodiment of the present invention.

FIG. 2 is a schematic diagram illustrating a more detail light sensing system according to one embodiment of the present invention. As illustrated in FIG. 2, the light sensor LS1 comprises light sensing units P1, P2. Please note other light sensing units are not illustrated or symbolized. The width for each of the sensing units is X, and the distance between center points of the sensing units is also X. In one embodiment, the X is 0.5 mm. For such structure, a difference between a distance from the light source L1 to the light sensing unit P1 and a distance from the light source L1 to the light sensing unit P2 is X, such that the light intensity which the light sensing unit P1 senses from the light source L1 and the light intensity which the light sensing unit P2 senses from the light source L1 are different. Therefore, even if the light sensing units P1, P2 have the same exposure conditions, the light sensing units P1, P2 receive different light amount in the same time period. Namely, the light source L1 causes different light responses to the light sensing units P1, P2. Accordingly, exposure conditions for the light sensing units P1, P2 must be different if the light source L1 is expected to cause the same light response to the light sensing units P1, P2.

Figure 3:
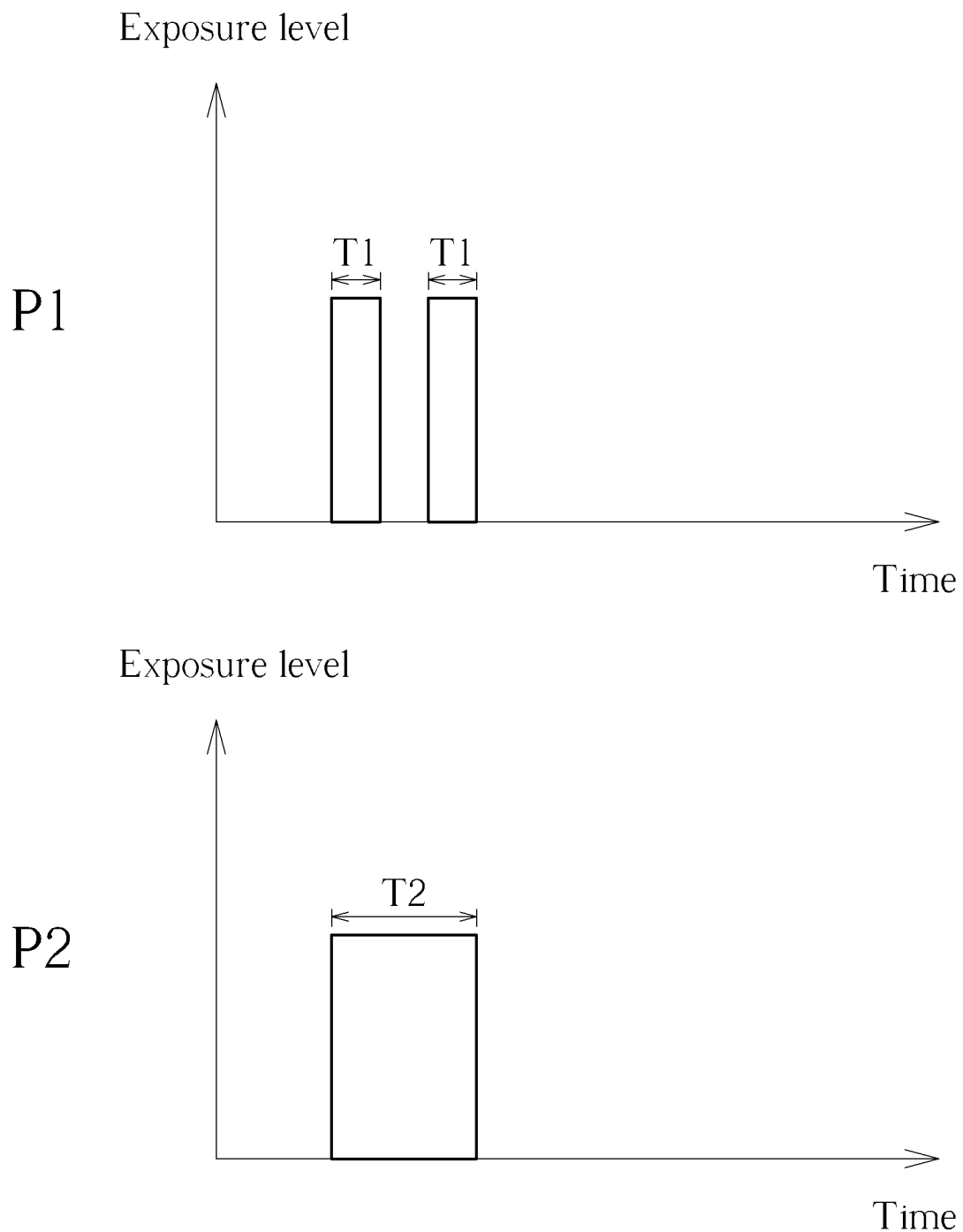
FIG. 3 is a schematic diagram illustrating how to control a light sensing time for light sensing units, according to one embodiment of the present invention.

FIG. 3 is a schematic diagram illustrating how to control a light sensing time for light sensing units, according to one embodiment of the present invention. As illustrated in FIG. 3, in this embodiment, the light sensing unit P1 is closer to the light source L1 and senses stronger light, thus is set to have a higher light sensing frequency but a shorter light sensing time T1 for each time of exposure. Oppositely, the light sensing unit P2 is farer from the light source L1 and senses weaker light, thus is set to have a lower light sensing frequency but a long light sensing time T2 for each time of exposure. That is, a light sensing frequency is inversely proportional to a distance between the light sensing unit and the light source, and a light sensing time is proportional to a distance between the light sensing unit and the light source. Please note, in one embodiment, either the light sensing frequency or the light sensing time is adjusted. In another embodiment, only one of the light sensing frequency and the light sensing time is adjusted. By this way, the exposure condition causes light amount that each of the light sensing units P1, P2 receives from the first light source L1 in a predetermined time period is a predetermined light amount. In other words, the light responses that the first light source L1 cause to the light sensing units P1, P2 are the same.

In above-mentioned embodiments, each of the light sensing units P1, P2 receives from the first light source L1 in a predetermined time period is a predetermined light amount, which means the light sensing system operates in a uniform mode. However, the light sensing system can operate in a non-uniform mode as well. In another embodiment, the exposure condition causes light amounts that different light sensing units receive from the first light source in a predetermined time period are different. Namely, the exposure condition causes light amount that the light sensing unit P1 receives from the first light source L1 in a predetermined time period is a first predetermined light amount, and cause light amount that the second light sensing unit P2 receives from the first light source L1 in the predetermined time period is a second predetermined light amount. The first predetermined light amount and the second predetermined light amount are different. That is, the light source L1 causes predetermined but different light responses to different light sensing units.

Figure 4:
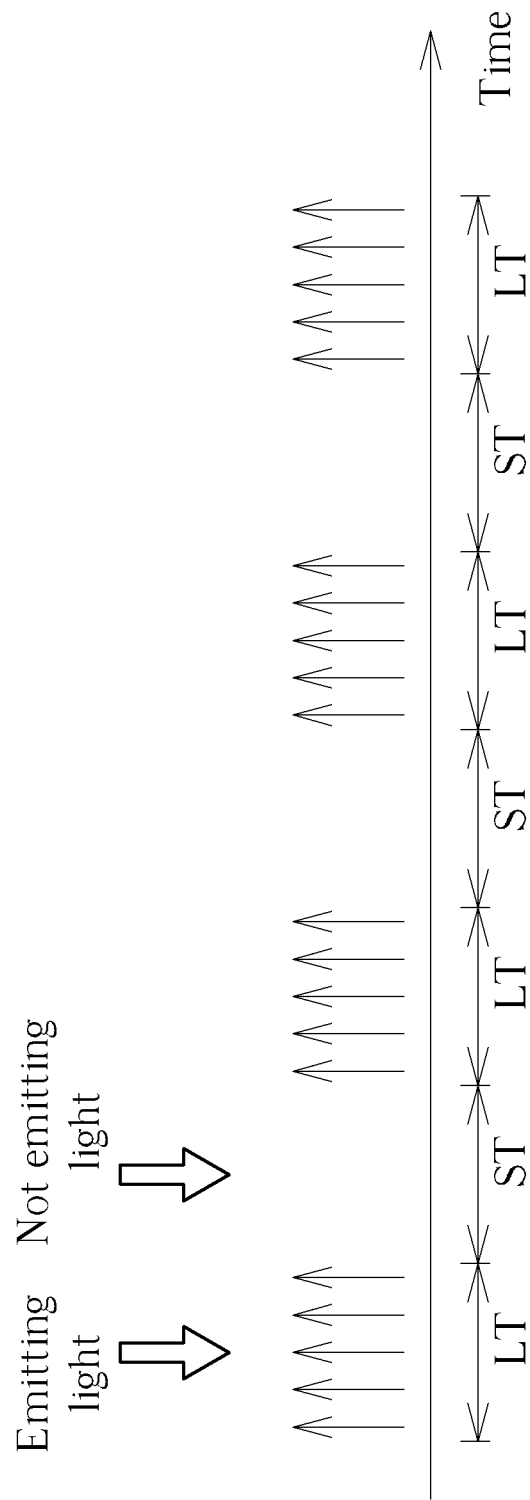
FIG. 4 is a schematic diagram illustrating that the light sensing system operates in a power saving mode.

The present invention also provides a power saving method, which can control the light sensing system to operate in a power saving mode. FIG. 4 is a schematic diagram illustrating that the light sensing system operates in a power saving mode. As illustrated in FIG. 4, the light source emits light for a plurality of times in a light emitting time LT, for example continuously emits light for a plurality of times, and does not emit light in a stop time ST consecutively following the light emitting time LT, and then emits light for a plurality of times in another light emitting time LT consecutively following the stop time ST. Lengths of the light emitting time LT, the stop time ST, and a number for emitting light can be set to any desired value. For a conventional light emitting method, the light source continuous emits light, and is activated for each time of light emitting. However, the light source enters a non-active state after emits light, and must be activated again for the next time of light emitting. Therefore, the conventional light emitting method consumes much power. Via the light emitting method in FIG. 4, the number for activating the light source can be decreased, thus the power consumption can be reduced.

Figure 5:
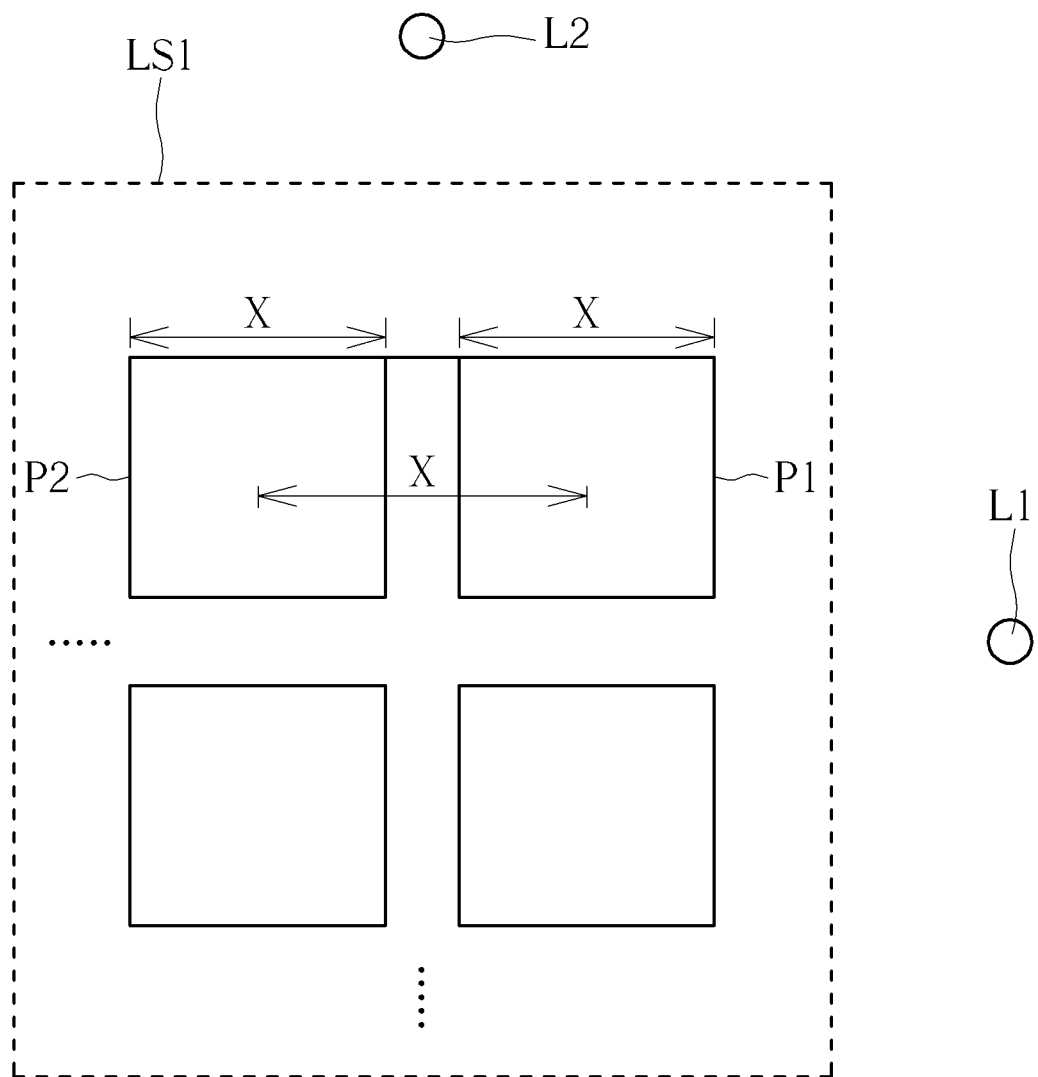
FIG. 5 is a schematic diagram illustrating how to control a light sensing time for light sensing units, according to one embodiment of the present invention.

In above-mentioned embodiments, a single light source is taken as an example for explaining. However, the light sensing method provided by the present invention can apply more than light sources. FIG. 5 is a schematic diagram illustrating how to control a light sensing time for light sensing units, according to one embodiment of the present invention. As illustrated in FIG. 5, the light sensor LS1 comprises light sensing units P1, P2, and the light sensing system comprises a plurality of light sources L1 and L2. In one embodiment, the light sensing system operates in a uniform mode, which means exposure condition causes light amount that each of the light sensing units P1, P2 receives from the first light source L1 in a predetermined time period is a predetermined light amount, and causes each of the light sensing units P1, P2 receives from the second light source L2 in the predetermined time period is also the predetermined light amount. That is, the exposure conditions for the light sensing units P1, P2 cause the light sources L1, L2 to generate the same light response to the light sensing units P1, P2.

In another embodiment, the light sensing system operates in a non-uniform mode. In such embodiment, the exposure condition causes light amount that each of the light sensing units receives from the first light source L1 in a predetermined time period is a first predetermined light amount, and cause light amount that each of the light sensing units receives from the second light source L2 in the predetermined time period is a second predetermined light amount. That is, the exposure conditions for the light sensing units P1, P2 cause the light sources L1, L2 to generate different light responses to the light sensing units P1, P2.

The light source can cause the same light response to different light sensing units in the uniform mode, such that the SNR can be raised. Also, the light sensing system can have better SNRs for different states in the non-uniform mode. Take the embodiment in FIG. 5 for example, the light sensing system senses stronger environment light while in an outdoor environment, thus the light source L1 is set to emit stronger light and the exposure condition is adjusted following above-mentioned rules. By this way, the light source L1 causes a proper light response to the light sensor LS1. In another example, the light sensing system senses weaker environment light while in an indoor environment, thus the light source L2 is set to emit weaker light and the exposure condition is adjusted following above-mentioned rules. By this way, the light source L2 causes a proper light response to the light sensor LS1.

In summary, the non-uniform mode causes the light sensing system provided by the present invention can operate smoothly in different environments. Also, the non-uniform mode can make sure that at least one light source causes proper light response to the light sensor, thus the application range for the light sensing system provided by the present invention can be extended.

Figure 6:
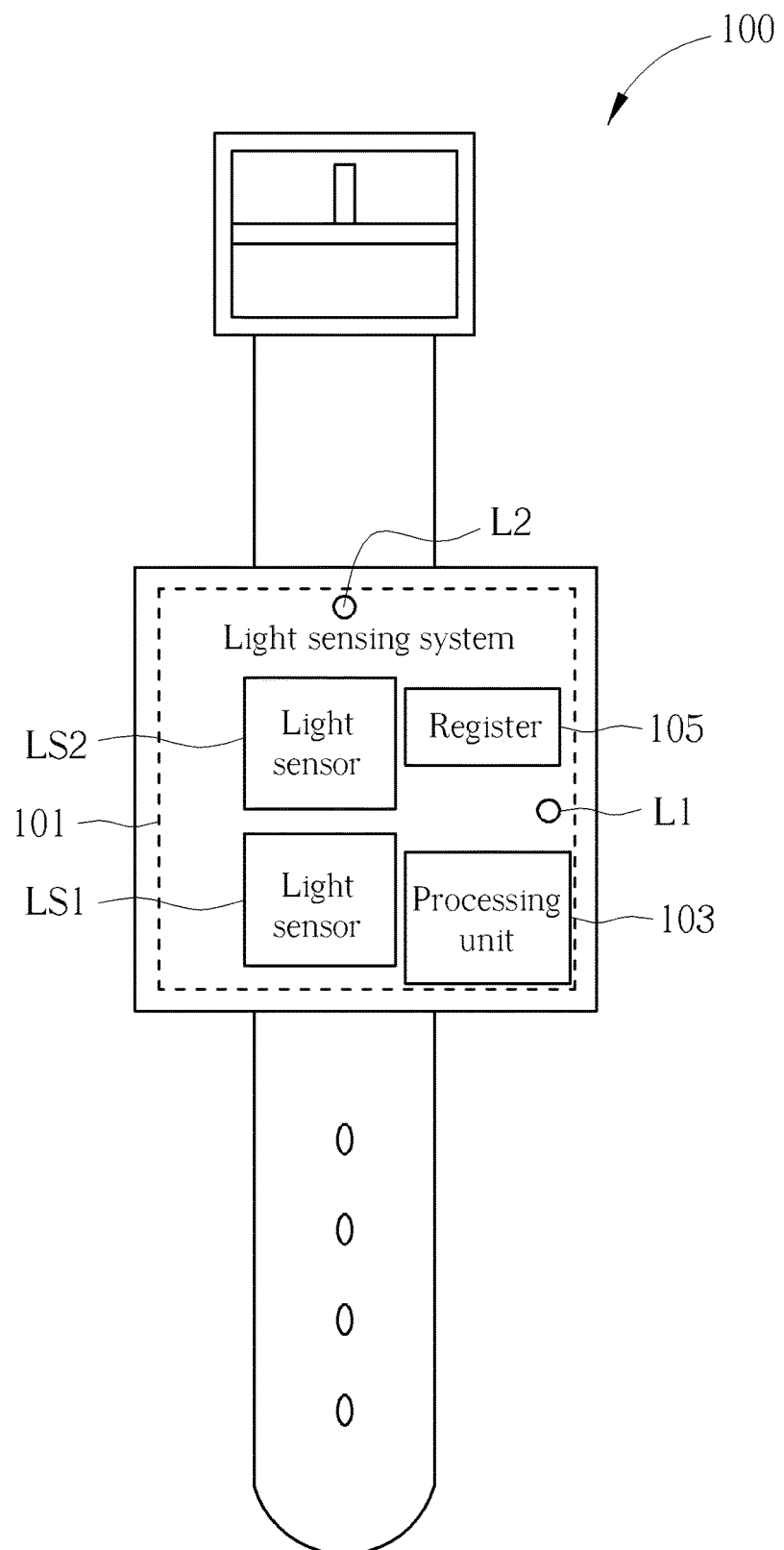
FIG. 6 is a schematic diagram illustrating a light sensing system according to another embodiment of the present invention.

In above-mentioned embodiments, a single light sensor is taken as an example for explaining. However, the light sensing system provided by the present invention can also comprise a plurality of light sensors and a plurality of light sources. FIG. 6 is a schematic diagram illustrating a light sensing system according to another embodiment of the present invention. Comparing with the embodiment in FIG. 1, the embodiment in FIG. 6 further comprises a light sensor LS2 and a light source L2. In this embodiment, different light sensors sense different light sources at different timings. For more detail, the operation that the light sensor LS1 senses the light source L1, the operation that the light sensor LS1 senses the light source L2, the operation that the light sensor LS2 senses the light source L1, and the operation that the light sensor LS2 senses the light source L2 are performed at different timings. By this way, the interferences between sensing operations can be avoided.

In view of above-mentioned embodiments, a light sensing method can be acquired, which comprises following steps: A light sensing method, applied to a light sensing system comprising a first light sensor (ex. LS1 in FIG. 1) and at least one light source (ex. L1 in FIG. 1). The first light sensor comprises a plurality of light sensing units (ex. P1, P2 in FIG. 2). The light sensing method comprises: (a) respectively controlling an exposure condition for each of the light sensing units according distances between each one of the light sensing units and the light source; and (b) controlling the light sensing units to sense the light from the light source according to the exposure condition.

The above-mentioned light sensing method can be applied to measure a heart-rate, but also can be applied to measure other physiological parameters such as a degree of blood oxygen. Therefore, a physiological parameter computing method according to the above-mentioned light sensing method can be acquired, which further comprises a following step (c) besides the above-mentioned steps (a) and (b). The step (c) is: computing a physiological parameter of a user according to light that the light sensing units senses in the step (b). If the apparatus comprising the apparatus provided by the present invention (ex. the wearable apparatus 100 in FIG. 1) performs such physiological parameter computing method, the apparatus can be regarded as a physiological parameter computing system. Besides, the step (c) can be performed by the processing unit 103 illustrated in FIG. 1.

In view of above-mentioned embodiments, the exposure conditions for each of the light sensing units can be adjusted to cause the light source to provide a proper light response to the light sensor. By this way, the SNR can be raised, and the accuracy for computing a physiological parameter can be increased as well. Additionally, the present invention further provides a power saving mode to save power consumption.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A light sensing method, applied to a light sensing system comprising a light sensor and at least one light source, wherein the light sensor comprises a plurality of light sensing units, the light sensing method comprising:

controlling the light sensor to capture images according to the light source;

adjusting an exposure condition to an adjusted exposure condition for each of the light sensing units, according brightness that each of the light sensing units senses, to control all the light sensing units to generate a target brightness distribution according to the adjusted exposure condition; and controlling the light sensing units to sense light from the light source according to the adjusted exposure conditions;

wherein the step of adjusting the exposure condition adjusts the exposure condition via adjusting at least one of: a light sensing time of the light sensing units, a light sensing frequency of the light sensing units and a gain value for light sensing signals read from the light sensing units.

2. A physiological parameter computing method applied to a physiological parameter computing system comprising a light sensing system including a plurality of light sensing units and at least one light source, wherein the physiological parameter computing method comprises:

controlling the light sensor to capture images according to the light source;

adjusting an exposure condition to an adjusted exposure condition for each of the light sensing units, according brightness that each of the light sensing units senses, to control all the light sensing units to generate a target brightness distribution according to the adjusted exposure condition; and controlling the light sensing units to sense light from the light source according to the adjusted exposure conditions;

wherein the step of adjusting the exposure condition adjusts the exposure condition via adjusting at least one of: a light sensing time of the light sensing units, a light sensing frequency of the light sensing units and a gain value for light sensing signals read from the light sensing units.

3. A light sensing system, comprising:

a plurality light sensing units;

at least one light source; and a processing unit, configured to adjust an exposure condition to an adjusted exposure condition for each of the light sensing units, according brightness that each of the light sensing units senses, to control all the light sensing units to generate a target brightness distribution according to the adjusted exposure condition;

wherein the light sensing units sense light from the light source according to the adjusted exposure conditions;

wherein the processing unit adjusts the exposure condition via adjusting at least one of: a light sensing time of the light sensing units, a light sensing frequency of the light sensing units and a gain value for light sensing signals read from the light sensing units.

* * * * *